United States Patent
Lee et al.

(10) Patent No.: US 7,628,533 B2
(45) Date of Patent: Dec. 8, 2009

(54) SYSTEMS AND METHODS FOR DETECTING CORROSION

(75) Inventors: Chung E. Lee, Austin, TX (US); William Hallidy, Austin, TX (US)

(73) Assignee: SensorTran, Inc, Austin, TX (US)

( * ) Notice: Subject to any disclaimer, the term of this patent is extended or adjusted under 35 U.S.C. 154(b) by 3 days.

(21) Appl. No.: 11/876,511

(22) Filed: Oct. 22, 2007

(65) Prior Publication Data

US 2008/0048103 A1    Feb. 28, 2008

Related U.S. Application Data

(63) Continuation-in-part of application No. 11/685,637, filed on Mar. 13, 2007.

(60) Provisional application No. 60/781,833, filed on Mar. 13, 2006, provisional application No. 60/787,617, filed on Mar. 30, 2006.

(51) Int. Cl.
   *G01N 25/00* (2006.01)
   *G01J 5/00* (2006.01)
   *G01K 11/00* (2006.01)

(52) U.S. Cl. .................. 374/7; 374/121; 374/161; 374/131; 374/45

(58) Field of Classification Search .............. 374/161, 374/131, 121, 45, 7
   See application file for complete search history.

(56) References Cited

U.S. PATENT DOCUMENTS

| | | | |
|---|---|---|---|
| 4,459,044 A * | 7/1984 | Alves | 374/131 |
| 4,560,286 A * | 12/1985 | Wickersheim | 374/131 |
| 4,752,141 A * | 6/1988 | Sun et al. | 374/161 |
| 4,823,166 A * | 4/1989 | Hartog et al. | 356/44 |
| 4,830,513 A * | 5/1989 | Grego | 374/131 |
| 4,859,079 A * | 8/1989 | Wickersheim et al. | 374/131 |
| 5,113,277 A | 5/1992 | Ozawa et al. | 359/127 |
| 5,191,206 A * | 3/1993 | Boiarski et al. | 250/227.14 |
| 5,302,025 A * | 4/1994 | Kleinerman | 374/131 |
| 5,765,948 A * | 6/1998 | Sai | 374/161 |
| 5,820,265 A * | 10/1998 | Kleinerman | 374/137 |
| 5,825,804 A * | 10/1998 | Sai | 374/137 |
| 5,991,479 A * | 11/1999 | Kleinerman | 385/31 |
| 6,380,534 B1 * | 4/2002 | Farhadiroushan et al. | 250/227.14 |
| 6,383,815 B1 * | 5/2002 | Potyrailo | 436/2 |
| 7,057,714 B2 | 6/2006 | Fredin et al. | 356/73.1 |
| 2004/0150827 A1 * | 8/2004 | Potyrailo et al. | 356/432 |
| 2005/0140966 A1 | 6/2005 | Yamate et al. | 356/72.1 |
| 2006/0210269 A1 * | 9/2006 | Farhadiroushan et al. | 398/48 |

FOREIGN PATENT DOCUMENTS

WO    2004/104536    12/2004

* cited by examiner

*Primary Examiner*—Gail Verbitsky
*Assistant Examiner*—Mirellys Jagan
(74) *Attorney, Agent, or Firm*—M. A. Ervin & Associates; Michael A. Ervin

(57) ABSTRACT

Systems and methods for detecting corrosion are provided. In one embodiment, a luminescent material coupled to a cladding of an optical fiber may be altered when exposed to corrosion. The backscatter emission of the luminescent material, which includes the altered optical properties, may be used to determine properties of the corrosion including, for example, thickness, or location of the corrosion.

8 Claims, 2 Drawing Sheets

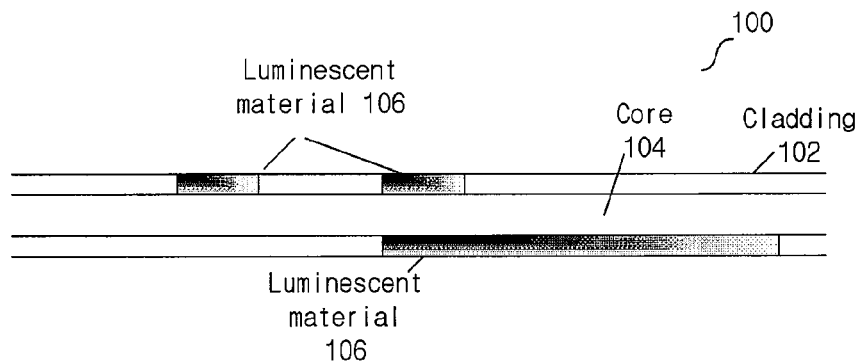
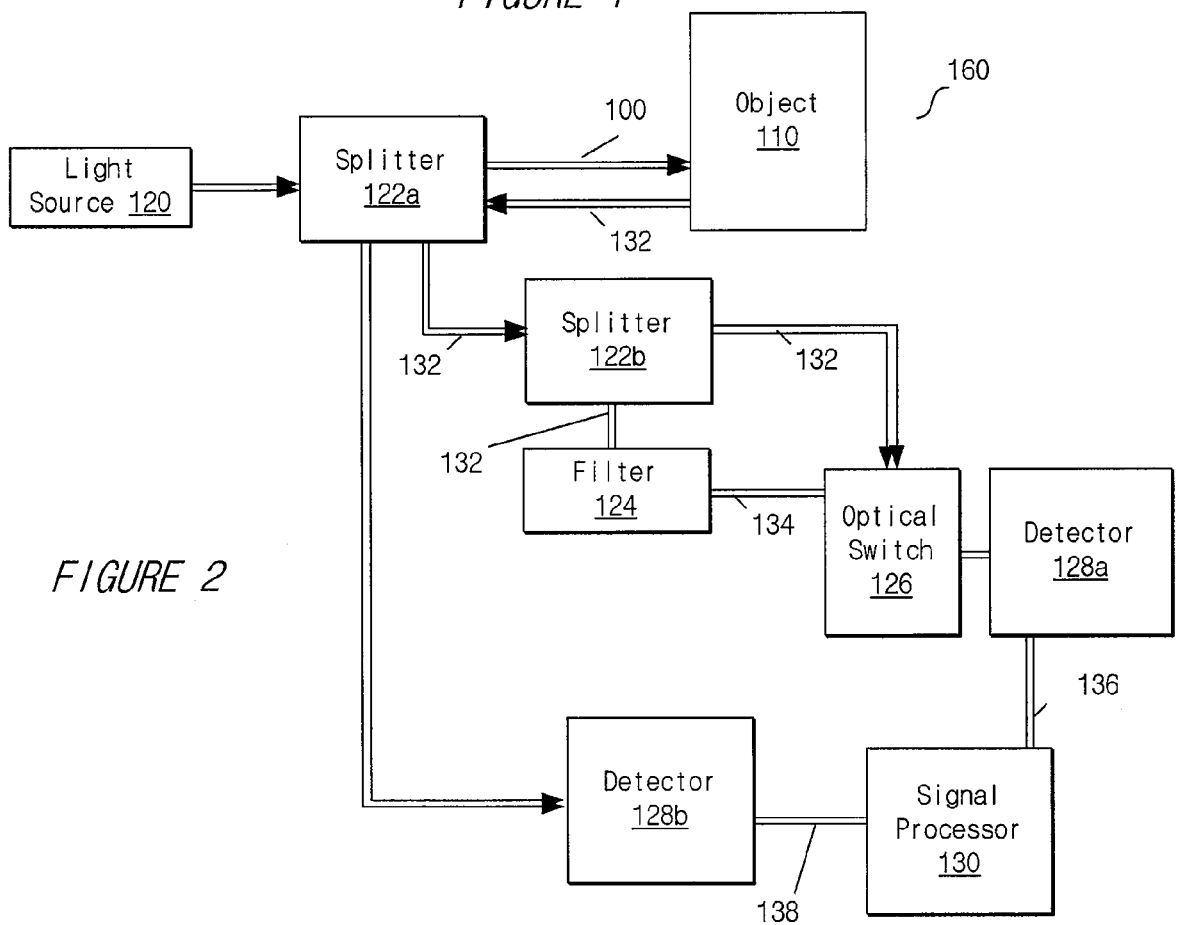

SYSTEMS AND METHODS FOR DETECTING CORROSION

RELATED PATENT APPLICATION

This application is a continuation-in-part application of U.S. patent application Ser. No. 11/685,637 filed Mar. 13, 2007 entitled "Methods and Apparatus for Dual Source Calibration for Distributed Temperature Systems"; which claims the benefit of U.S. Provisional Application No. 60/781,833 filed Mar. 13, 2006 and claims the benefit of U.S. Provisional Application No. 60/787,617 filed Mar. 30, 2006, the contents of which are hereby incorporated by reference in their entirety.

TECHNICAL FIELD

The present disclosure relates to corrosion detection, and more particularly, to a system and method for detection and measuring corrosion using an optical fiber sensor.

BACKGROUND

Reliable corrosion monitoring is important to reduce physical failures of components and reduce production costs and delays. Various attempts have been made using electrochemical (EC) and non-electrochemical techniques to identify corrosion processes. For example, linear polarization resistance (LPR) and electrochemical noise methods have been used to identify corrosion rates, types of corrosion, and parameters associated with localized corrosion. Other techniques include the application of electrical resistance (ER) measurements to determine loss of thickness and hence determine corrosion rates. However, these methods have not been entirely satisfactory in providing an unambiguous method to determine the propagation of localized corrosion in a robust and cost effective manner.

One of the problems encountered with currently available corrosion monitoring methods and devices is the lack of reliable measurements to determine uniform corrosion rate or the rate of localized corrosion. The LPR technique typically only provides information on uniform corrosion conditions because it provides an average signal for the surface of the electrode being monitored. Depending upon the environment, metallic material, and corrosion type, the assumption that the corrosion rate is proportional to the measured charge transfer or polarization resistance is invalid when the corrosion is of a localized nature. It is known that localized corrosion (e.g., pitting) is a leading cause of physical and/or mechanical failure. With LPR, the instantaneous corrosion rate may vary by several orders of magnitude over a short time. Moreover, due to the complex nature of the measurements and varying resistances involved, the rate at which the potential is scanned may have a significant effect on the amount of current produced. Such systems require precise measurements of small incremental changes in the electrical properties of the sensor device, thus making them quite susceptible to inaccuracy due to noise. Accordingly, such devices typically require relatively complex and expensive components to overcome the noise problems, substantially increasing the cost of making and using such devices.

A drawback of EC-type sensors is their considerable bulk due to the long length of the exposed strip necessary to make changes in resistance easily measurable. Although it may be possible to reduce the thickness of the strip, this will adversely affect the life of the sensor because a reduced sensor thickness will corrode in a shorter period of time.

SUMMARY

The present disclosure provides systems and methods for detecting corrosion. In one respect, a method for detecting corrosion is provided. The method includes transmitting an electromagnetic radiation from a light source through an optical fiber comprising a luminescent material. The luminescent material may interact with corrosion of an object, which may alter the optical properties of the luminescent material.

Next, the backscatter emission of the luminescent material is detected. The backscatter material may include optical properties related to the corrosion on the object. Using the optical properties (e.g., magnitude, flight time, intensity, etc.), the characteristics of the corrosion may be determined.

A system for detecting corrosion is also provided. The system may include an electromagnetic radiation source, such as a pulsed light source or a continuous light source.

In some embodiments, an optical fiber may be coupled to the electromagnetic radiation source and may be configured to propagate an emission from the electromagnetic radiation source to an object. The optical fiber may include a core, a cladding surrounding the core, and a luminescent material for interacting with corrosion of the object. In particular, the corrosion may alter the optical properties of the luminescent material, and may be observed via a backscatter emission of the luminescent material.

The system may also include a plurality of detectors for detecting backscatter emission of the luminescent material. The detectors may be configured to convert the emission into electrical signals and may provide the electrical signals to a signal processor. The signal processor determining a location of the corrosion based at least on the detected backscatter emission.

Other technical advantages will be apparent to those of ordinary skill in the art in view of the following specification, claims, and drawings.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein:

FIG. 1 shows an optical fiber for detecting corrosion, in accordance with embodiments of the present disclosure.

FIG. 2 shows a block diagram of a system for detecting corrosion, in accordance with embodiments of the present disclosure.

DETAILED DESCRIPTION

Figure 3:
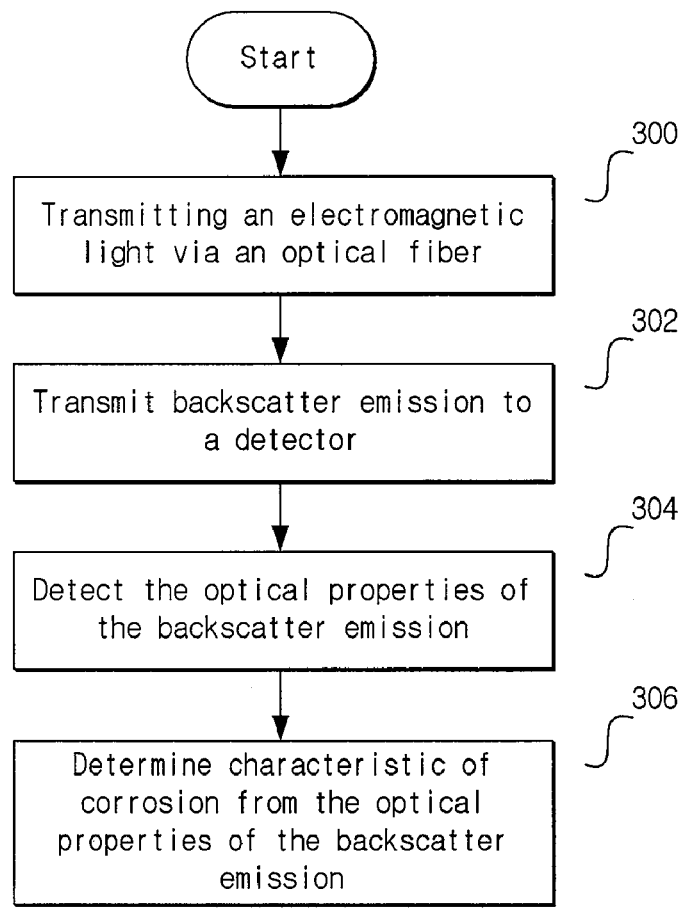
FIG. 3 shows a flowchart for detecting corrosion, in accordance with embodiments of the present disclosure.

Preferred embodiments and their advantages are best understood by reference to FIGS. 1 through 4B, wherein like numbers are used to indicate like and corresponding parts.

An optical fiber, as used and define herein, refers to a material (e.g., glass, plastic, etc.) that may guide light along the length of the material. An optical fiber may be used as a sensor to measure certain parameters including, but not limited to, corrosion, thickness, size, and the like.

The present disclosure provides distributed sensor systems and methods for detecting, locating, and measuring corrosion using an optical fiber having a luminescent material. In one embodiment, the optical fiber may be placed in the near vicinity and/or may be coupled to an object under test. This allows for areas that are not generally accessible (e.g., due to the location) to be tested.

Referring to FIG. 1, an optical fiber 100 having a luminescent material is shown, in accordance with embodiments of the present disclosure. Optical fiber 100 may include a cladding 102 surrounding a core 104. Core 104 may have a refractive index capable of propagating light. Cladding 102, with a refractive index less than that of core 104 may be used to maintain a total internal reflection of the propagating light, thus allowing light to traverse the entire length of optical fiber 100 without any significant loss.

In one embodiment, optical fiber 100 may include a luminescent material 106. A portion of cladding 102 may be stripped and luminescent material 106 may be deposited into core 104 and/or may be distributed through cladding 102. In other embodiments, alternatively or in addition, the luminescent material 106 may be deposited at discrete sections along fiber 100. Luminescent material 106 may include a fluorophore layer or other suitable material. Optical fiber 100 may also include a transparent porous protection layer such as SolGel surrounding cladding 102 and luminescent material.

FIG. 2 illustrates an example system 160 for detecting, locating, and/or measuring corrosion on an object 110 using optical fiber 100, in accordance with embodiments of the present disclosure. Object 110 may include any device, component, machinery, or other items that may be susceptible to corrosion or is suspected to have corrosion. Optical fiber 100 may be placed directly onto object 110 or alternatively, may be place within the vicinity of object 110.

System 160 may include an electromagnetic light source 120, splitters 122a and 122b, a filter 124, detectors 128a and 128b, and signal processor 130. Light source 120 may comprise any continuous or pulsed electromagnetic radiation source configured to provide emit light in a visible spectrum or outside a visible spectrum through optical fiber 100. For example, light source 120 may be a pulsed ultra violet laser. The light emitted from light source 120 may travel through optical fiber 100 to object 110. Luminescent material 106 may interact with corrosion material and may change the emission of luminescent material 106 including changes in the intensity and/or peak wavelength. The changes to luminescent material may be seen in the backscattering emission of the luminescent material.

Splitters 122a and 122b coupled to light source 120 may be configured to distribute light (e.g., light from the light source and/or the backscattering emission of luminescent material 106). In one embodiment, an optical energy or light from light source 120 may be transmitted to optical fiber 100 via splitter 122a. Luminescent material 106 of optical fiber 100 may interact with corrosion material of object 110 and may change the emission of luminescent material 106 including changes in the intensity and/or peak wavelength.

The changes to luminescent material (e.g., the optical properties) may be seen in the backscattering emission of the luminescent material. The backscattering emission 132 may be guided to splitter 122b via 122a.

Subsequently, splitter 122b may provide the backscatter emission 132 to filter 124 and optical switch 126. Filter 124 coupled to fiber splitter 122b may be used to filter the backscatter emission and provide the filtered backscatter emission 134 (e.g., fluorescent properties), which includes information relating to the corrosion of object 110 to optical switch 126.

Optical switch 126 coupled to fiber splitter 122b may be provided as input filtered backscatter emission 134 from filter 124 and backscatter emission 132 from splitter 122b. In one respect, optical switch 126 may be used to compensate the light variation made along optical fiber 100. With this configuration, the undesired optical energy variation due to source fluctuation and the loss changes induced from physical perturbation can be completely compensated.

Detector 128a receives as input either the filtered backscatter emission 134 or the backscatter 132 via optical switch 126. Detector 128a may be configured to convert either input into an electrical signal and may provide the electrical signal as output 136 to signal processor 130. Similarly, detector 128b, which receives the emission from light source 120 via splitter 122a may be configured to convert the emission to an electrical signal and provide the electrical signal as output 138 to signal processor 130.

Signal processor 130 coupled to detectors 128a and 128b may receive outputs 136 and 138 from detectors 128a and 128b, respectively. Signal processor 130 may receive a wavelength frequency of the backscatter emission from detector 128a which may be used to identify the location of the corrosion. In one embodiment, signal processor 130 may be configured similar to a spectrometer which may detect the backscatter emission (e.g., a wavelength shift) made by the corrosion. For example, signal processor 130 to measure properties of light over a specific portion of a light spectrum. Using conventional time domain or frequency domain technique, the location of the corrosion may be determined. For example, using the length of optical fiber 100 and the time a light travels round trip (e.g., detected by a sensor or other similar sensing technique known in the art), the location of the corrosion may be determined.

Signal processor 130 may also determine the magnitude of corrosion. A voltage output from the signal processor may measure may be used to determine the amplitude and peak wavelength of the backscatter emission.

FIG. 3 illustrates an example flowchart of a method for detecting corrosion, in accordance with embodiments of the present disclosure. At step 300, an electromagnetic radiation from electromagnetic light source 100 may be propagated via optical fiber 100. Optical fiber 100 may be placed in the vicinity of object 110 under test. In other embodiments, optical fiber 100 may be coupled to object 110 under test. Any corrosion on object 110 may interact with luminescent material 106 of optical fiber 100 and may alter the optical property (e.g., intensity and/or peak wavelength) of the luminescent material.

At step 302, the backscatter emission of the luminescent material, which includes the altered optical property, may be provided to detector 128a and/or detector 128b. In one embodiment, the backscatter emission may be filtered to select the optical properties relating to the backscatter emission, and in particular, the corrosion of object 110. The backscatter emission is discussed in more detail with respect to FIGS. 4A and 4B.

At step 304, detector 128a and/or detector 128b may detect the optical properties of the backscatter emission. In one embodiment, detectors 128a and/or 128b may determine, the flight time, the magnitude, and/or the average signal of the backscatter emission may be detected. Detector 128a may receive as input via switch 126 a filtered backscatter emission or the backscatter emission and detector 128b may receive a light emission from light source 120. The inputs of detectors 128a and 128b may be converted into an electrical signal and provided to signal processor 130.

At step 306, the properties of any corrosion on object 110 may be determined. In one embodiment, signal processor 130 may receive the optical properties of the backscatter emission from detectors 128a and/or 128b. Signal processor 130 may determine the location of the corrosion on object 110 using at least the flight time of the backscatter emission. Signal processor 130 may also determine the magnitude of the corrosion using at least the average signal of the backscatter emission.

In some embodiments, a compensating algorithm may be used to compensate for light intensities caused by light source 120, during the transmission of the backscatter emission to detector 128a and/or 128b.

Figure 4A:
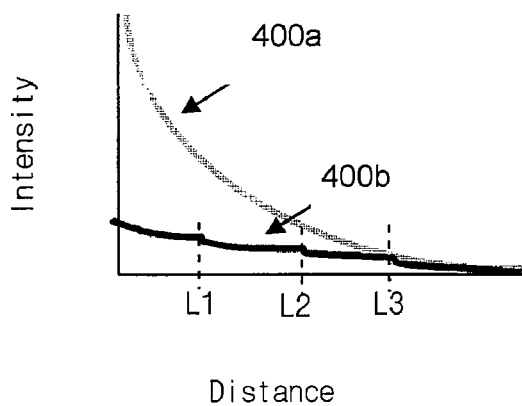
FIGS. 4A and 4B show backscatter emission in an optical fiber, in accordance with embodiments of the present disclosure.
Figure 4B:
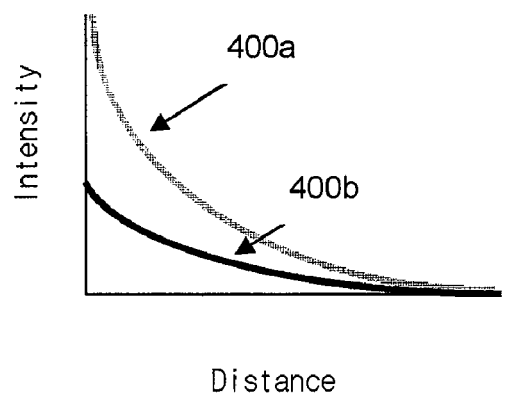

FIG. 4A illustrates a backscatter emission 400a from luminescent material 106 when there is corrosion present. The intensity of the luminescent intensity 402a and backscatter emission 400a is affected at different locations (L1, L2, and L3) where corrosion is present. This is compared to luminescent intensity 402b of FIG. 4B where no corrosion is detected.

Although the present disclosure has been described in detail, it should be understood that various changes, substitutions, and alterations can be made hereto without departing from the spirit and the scope of the invention as defined by the appended claims.

What is claimed is:

1. A distributed sensor system for locating and measuring corrosion on an object or objects on which a single line of optical sensing fiber is deployed in close proximity comprising:
   a. an electromagnetic radiation source for emitting an emission of light;
   b. an optical sensing fiber coupled to said electromagnetic radiation source, said optical sensing fiber illuminated by said electromagnetic radiation source and wherein said optical sensing fiber comprises:
      i. a core;
      ii. a cladding surrounding said core;
      iii. wherein a luminescent material is integrated into the cladding surrounding said core and provides a backscatter emission;
      iv. and wherein said luminescent material is selected to interact with corrosion chemicals so that the luminescent material's resulting backscatter emission changes in intensity and/or peak wavelength when exposed to corrosion of said object or objects;
   c. an optical filter used to filter the backscatter emission to provide a filtered backscatter emission;
   d. an optical switch that selects between the backscatter emission and the filtered backscatter emission;
   e. a first photo detector for receiving and measuring either the backscatter emission or the filtered backscatter emission;
   f. a second photo detector for receiving and measuring said emission of light;
   g. a bi-directional fiber splitter that provides the light path from said electromagnetic radiation source to said line of optical sensing fiber and the light path from said backscatter emission to said photo detectors; and
   h. a signal processor for receiving outputs from said first and second detectors for determining corrosion location and magnitude.

2. The distributed sensor system for locating and measuring corrosion of claim 1 wherein said luminescent material in said optical sensing fiber is continuously integrated into the complete length of cladding of said optical sensing fiber.

3. The distributed sensor system for locating and measuring corrosion of claim 1 wherein said cladding surrounding said core is removed at discrete locations on the core and replaced with said luminescent material.

4. The distributed sensor system for locating and measuring corrosion of claim 1 wherein a porous protection layer is integrated onto a luminescent mixed cladding layer as the jacket of said optical fiber.

5. The distributed sensor system for locating and measuring corrosion of claim 1 wherein outputs from said first detector is fed to said signal processor and used to locate the corrosion source along the fiber by determining the flight time of said filtered backscatter emission.

6. The distributed sensor system for locating and measuring corrosion of claim 1 wherein outputs from said first detector and said second detector are fed to said signal processor and used to determine the magnitude of corrosion by measuring the average signal from said backscatter emission.

7. The distributed sensor system for locating and measuring corrosion of claim 6 wherein a compensating algorithm is used to correct for errors due to undesired variation of backscattered light intensities occurring from fiber connections, fiber bending, and the light of primary emission.

8. A method for detecting, locating, and measuring corrosion along the length of an object or objects on which a single line of optical sensing fiber is deployed in close proximity comprising the steps of:
   a. providing an optical sensing fiber comprising a core, and a cladding surrounding said core,
   b. providing a luminescent material integrated into the cladding surrounding said core; said luminescent material selected to interact with corrosion chemicals so that the luminescent material's emissions change in intensity and/or peak wavelength when exposed to corrosion;
   c. deploying said optical sensing fiber in proximity to said object or objects;
   d. illuminating said optical sensing fiber with a wavelength of light;
   e. collecting backscatter emissions from said optical sensing fiber;
   f. separating said backscatter emissions into a backscatter emission and a filtered backscatter emission;
   g. providing photo detectors to measure wavelengths and intensities of said wavelength of light, and said backscatter emission and filtered backscatter emission; and
   h. providing the outputs from said photo detectors to a signal processor that:
      i. compensates for calculation errors due to undesired variation of backscatter light intensities occurring from fiber connections, bending of the sensing fiber, and the wavelength of light; and
      ii. utilizes the resulting error compensated outputs to determine corrosion location and magnitude.

* * * * *